United States Patent
Iitsuka et al.

(10) Patent No.: US 12,257,220 B2
(45) Date of Patent: Mar. 25, 2025

(54) COMPOSITION FOR IMPROVING ENDURANCE AND METHOD OF IMPROVING ENDURANCE USING THE SAME

(71) Applicants: PHARMA FOODS INTERNATIONAL CO., LTD., Kyoto (JP); KYOTO PREFECTURAL PUBLIC UNIVERSITY CORPORATION, Kyoto (JP)

(72) Inventors: Hiroaki Iitsuka, Kyoto (JP); Yugweng Kim, Kyoto (JP); Maya Sakashita, Kyoto (JP); Atsushi Yamatsu, Kyoto (JP); Mujo Kim, Kyoto (JP); Wataru Aoi, Kyoto (JP)

(73) Assignees: PHARMA FOODS INTERNATIONAL CO., LTD., Kyoto (JP); KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 0 days.

(21) Appl. No.: 17/179,943

(22) Filed: Feb. 19, 2021

(65) Prior Publication Data

US 2021/0322352 A1 Oct. 21, 2021

(30) Foreign Application Priority Data

Feb. 21, 2020 (JP) .................................. 2020-28755

(51) Int. Cl.
*A61K 31/197* (2006.01)
*A23L 33/17* (2016.01)
*A61P 21/00* (2006.01)

(52) U.S. Cl.
CPC ............ *A61K 31/197* (2013.01); *A23L 33/17* (2016.08); *A61P 21/00* (2018.01)

(58) Field of Classification Search
CPC ....... A61K 31/197; A23L 33/17; A23L 33/10; A61P 21/00
See application file for complete search history.

(56) References Cited

U.S. PATENT DOCUMENTS 10,548,865 B1 * 2/2020 Ouyang .................. A61P 21/06

FOREIGN PATENT DOCUMENTS

| CN | 105614612 | * | 6/2016 |
| CN | 105614612 A | * | 6/2016 |
| JP | 2004269361 A | | 9/2004 |

(Continued)

OTHER PUBLICATIONS

Kanehira T, Nakamura Y, Nakamura K, Horie K, Horie N, Furugori K, Sauchi Y, Yokogoshi H. Relieving occupational fatigue by consumption of a beverage containing γ-amino butyric acid. J Nutr Sci Vitaminol (Tokyo). 2011;57(1):9-15. (Year: 2011).*

(Continued)

*Primary Examiner* — Bethany P Barham
*Assistant Examiner* — Janet Joseph
(74) *Attorney, Agent, or Firm* — Renner, Otto, Boisselle & Sklar, LLP

(57) ABSTRACT

[Technical Problem]
To provide a novel composition for more efficiently improving endurance than the conventional art.
[Solution to Problem]
A composition for improving endurance, comprising γ-aminobutyric acid.

13 Claims, 9 Drawing Sheets

(56) References Cited

FOREIGN PATENT DOCUMENTS

| JP | 2007204406 A | 8/2007 |
|---|---|---|
| JP | 2008156294 A | 7/2008 |
| JP | 2009045034 A | 3/2009 |

OTHER PUBLICATIONS

Eyestone (Use Your Muscles to Run Train yourself to run with more muscle and you could go further and faster than you ever thought possible) . Published: May 23, 2007 (Year: 2007).*
Kook, MC., Cho, SC., Kang, J. et al. Effect of gamma-aminobutyric acid produced by Lactobacillus sakei B2-16 on diet and exercise in high fat diet-induced Obese rats. Food Sci Biotechnol 23, 1965-1970 (2014). https://doi.org/10.1007/s10068-014-0268-0 (Year: 2014).*
PharmaGABA-100, Thorne (Dec. 4, 2019). https://www.thorne.com/products/dp/pharmagaba-100?gad_source=1&gclid=CjwKCAiA_5WvBhBAEiwAZtCU737r_V5mztEFapv6Ne1mqsZ6ohFHorwkA7G8SQ9iIQLETuYJTL2mbxoCLykQAvD_BwE (Year: 2019) (Year: 2018).*
Powers, Michael E.1; Yarrow, Joshua F.2,3; McCoy, Sean C.2; Borst, Stephen E.2,3. Growth Hormone Isoform Responses to GABA Ingestion at Rest and after Exercise. Medicine & Science in Sports & Exercise 40(1):p. 104-110, Jan. 2008. | DOI: 10.1249/mss.0b013e318158b518 (Year: 2008).*
Penney, S. (Dec. 2, 2020.). Fast-twitch vs. slow-twitch muscle fiber types + training tips. NASM. https://blog.nasm.org/fitness/fast-twitch-vs-slow-twitch#:~:text=Fast%20Twitch%20Muscle%20Fiber%20Types,such%20as%20sprinting%20or%20weightlifting. (Year: 2020).*
Metabolic equivalent (met): Pick the best exercise for longevity. whyiexercise.com. (May 2018.). https://www.whyiexercise.com/metabolic-equivalent.html (Year: 2018).*
Third Party Observation for corresponding Japanese Application No. 2021-025423 mailed Mar. 25, 2024.
J. Clin. Med. Res. (2019) vol. 11, No. 6, p. 428-434.
F. Cavagnini et al., Acta Endocrinologica 1980, 93, 149-154.

* cited by examiner

COMPOSITION FOR IMPROVING ENDURANCE AND METHOD OF IMPROVING ENDURANCE USING THE SAME

TECHNICAL FIELD

The present disclosure is directed to a composition for improving endurance and a method of improving endurance using the same.

BACKGROUND ART

Improvement of endurance is essential in order to build a body that hardly feels fatigue and achieve faster recovery from fatigue in all physical activities such as every-day activities, for instance, domestic chores, walking to commute and hobbies carried out during free time, not to mention sports competitions that require exercise for a long time. Thus, it is desirable to enable long-term energy supply by increasing cardiopulmonary function as the same time ascreating more energy by developing capillaries of a muscle or increasing the amount of blood flowing in a muscle (muscle blood flow rate), by continuing to exercise on a daily basis.

Meanwhile, while it is widely known in modern society that continuous exercise is desirable for improving endurance or health, automization of domestic chores and work and as well as in transportation have reduced the amount of physical activity and caused a low proportion of people who actually carry out continuous exercise. Furthermore, in addition to the reduction in the amount of physical activity, change in eating habits is a contributing factor to the recent increase in lifestyle-related diseases. Furthermore, improvement of endurance by exercise does not achieve a sufficient effect in a short period of time but requires repetition of exercise for a long period of time. Thus, an injury related to long-term exercise or difficulty in feeling the effect of the training is a factor in being unable to continue exercise.

Therefore, efficient improvement of endurance by training is not only important for sports players who require endurance, but also many people can continue exercising without becoming overly stressed.

SUMMARY OF INVENTION

Technical Problem

The present invention was invented in view of such a circumstance, and for the purpose of providing a new composition for improving endurance more efficiently than before.

Solution to Problem

The inventors of the present invention carried out several earnest studies to solve the above-described problem and as a result confirmed that γ-aminobutyric acid (GABA) enhances the effect of improving endurance and achieved completion of the present invention by carrying out further study based on said finding.

Therefore, according to the major points of the present disclosure, the following inventions are provided.
(A1) A composition for improving endurance comprising γ-aminobutyric acid.
(A2) The composition of the item above, wherein a content of the γ-aminobutyric acid is about 10 mg or more.
(A3) The composition of any one of the items above, which is turned into a dosage form or in a packaged form so as to comprise about 10 to about 2000 mg per day of the γ-aminobutyric acid.
(A4) The composition of any one of the items above, which is orally ingested.
(A5) The composition of any one of the items above, which is for ingestion upon a training.
(A6) The composition of item (A5), which is ingested prior to initiation of a training, during a training, or after termination of a training.
(A7) The composition of item (A5) or (A6), which is for enhancing an effect of improving endurance by a training.
(A8) The composition of any one of the items above, which is a composition for improving muscle endurance.
(A9) The composition of any one of the items above, which is for enhancing an amount of glycogen in a skeletal muscle.
(A10) The composition of any one of the items above, which is for promoting glycogen loading in a skeletal muscle.
(A11) The composition of any one of the items above, which is for reducing an amount of insulin in plasma.
(A12) The composition of any one of the items above, which is for suppressing phosphorylation of protein kinase B (Akt) in a skeletal muscle.
(A13) The composition of any one of the items above, which is for increasing an amount of expression of PGC-1α in a skeletal muscle.
(A14) The composition of any one of the items above, which is for increasing an amount of expression of AMPK protein in a skeletal muscle.
(A15) The composition of any one of the items above, which is for increasing an amount of expression of myosin protein in a skeletal muscle.
(A16) The composition of any one of the items above, which is for increasing an amount of expression of myosin heavy chain (MHC) 2a.
(A17) The composition of any one of the items above, which is for enhancing an amount of slow muscle in a skeletal muscle.
(A18) The composition of any one of the items above, which is for enhancing a type I muscle fiber in a skeletal muscle.
(A19) The composition of any one of the items above, which is for enhancing a type IIa muscle fiber in a skeletal muscle.
(A20) The composition of any one of the items above, which is a drinking/eating product, a food additive, a quasi-drug, or a medicament.

In addition, according to the other major viewpoints of the present disclosure, the following inventions are also provided.
(B1) A non-therapeutic method of improving endurance, having the step of ingesting the composition of any one of the items above.
(B2) The method of item (B1), wherein a content of the γ-aminobutyric acid is about 10 mg or more.
(B3) The method of item (B1) or (B2), wherein about 10 to about 2000 mg per day of the γ-aminobutyric acid is ingested.
(B4) The method of any one of items (B1) to (B4), wherein the composition is orally ingested.
(B5) The method of any one of items (B1) to (B5), wherein the composition is ingested upon a training.
(B6) The method of item (B5), wherein the composition is ingested before initiation of a training, during a training, or after termination of a training.
(B7) The method of item (B5) or (B6), wherein the composition is ingested to enhance an effect of improving endurance by a training.

In addition, according to the other major viewpoints of the present disclosure, the following inventions are also provided.

(C1) A method of improving endurance, having the step of ingesting the composition of any one of the items above.
(C2) The method of item (C1), wherein a content of the γ-aminobutyric acid is about 10 mg or more.
(C3) The method of item (C1) or (C2), wherein about 10 to about 2000 mg per day of the γ-aminobutyric acid is ingested.
(C4) The method of any one of items (C1) to (C4), wherein the composition is orally ingested.
(C5) The method of any one of items (C1) to (C5), wherein the composition is ingested upon a training.
(C6) The method of item (C5), wherein the composition is ingested before initiation of a training, during a training, or after termination of a training.
(C7) The method of item (C5) or (C6), wherein the composition is ingested to enhance an effect of improving endurance by a training.

The characteristics and significant actions/effects of the present disclosure that are not described above would be clear to those skilled in the art by seeing the following embodiment section and drawings of the invention.

BEST MODE FOR CARRYING OUT THE INVENTION

Figure 1:
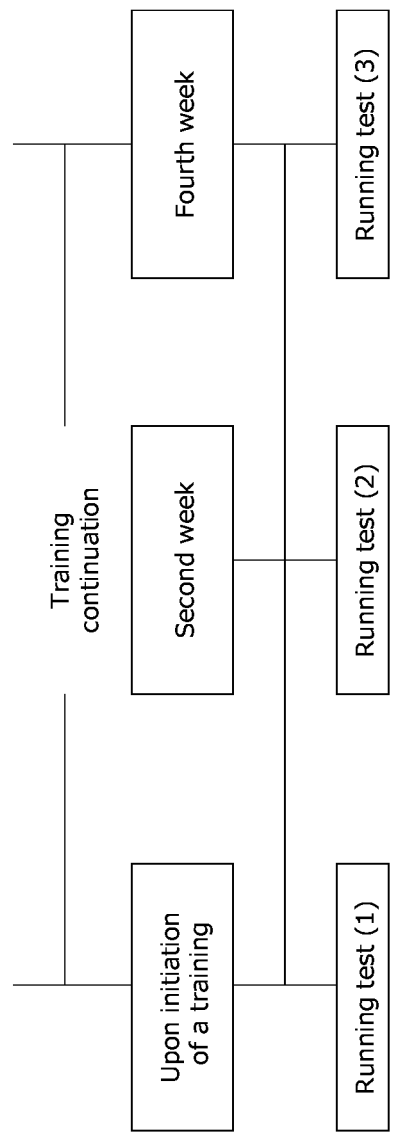
FIG. 1 is a schematic view showing a schedule of training and running test of one embodiment of the present disclosure.

One embodiment and example of the present disclosure are explained below while referring to the drawings.

As described above, one embodiment of the present disclosure is a composition for improving endurance comprising γ-aminobutyric acid.

γ-aminobutyric acid (GABA, 4-aminobutyric acid) has been recently receiving attention as an amino acid that is widely distributed in the natural world and can be added to food without altering its taste. GABA is known to be a suppressive neurotransmitter, many of which exist in a central nervous system of a mammal, suppressing excessive secretion of excitatory neurotransmitter to relieve excitation of a nerve, thus exerting a relaxing effect or anti-stress action. In addition, it is known to have various physiological activities such as lowering blood pressure, reducing blood cholesterol concentration, and suppressing reduction of immunity. GABA is also found in vegetables, grain and human bodies, and can thus easily be added to food. Chocolates and many supplements comprising GABA are sold.

Ingestion of GABA in addition to whey protein that stimulates skeletal muscle hypertrophy stimulates more muscle hypertrophy as compared to the case of whey protein alone and also increases of the amount of fat removed muscle, which is reported as an effect of GABA ingestion in training (J Clin Med Res. 2019; 11(6):428-434). Meanwhile, it is publicly known that the performance regarding endurance does not improve even if a steroid having a muscle hypertrophic effect is ingested (e.g., Eur. J. Appl. Physiol. November 2006, Vol. 98, Issue 4, pp 329-340). Muscle hypertrophy and improvement of endurance are phenomenons with different properties and mechanisms.

Since GABA is an amino acid widely distributed in the natural world such as in vegetables and grain, the origin or the like of GABA is not particularly limited as long as it can be used in drinks or food in one embodiment of the present disclosure. For example, an extract, a purified product, or the like of a plant comprising GABA may be used, or it is possible to carry out preparation from a fermented product obtained by adding glutamic acid decarboxylase, a microorganism having said enzyme such as lactic acid bacteria, or the like to a raw material comprising glutamic acid. A product comprising GABA or GABA of a commercially available product can also be a raw material of the composition of the present disclosure in the scope that does not harm the effect caused by the composition of the present disclosure.

In one embodiment of the present disclosure, as the timing of ingestion of a composition for improving endurance comprising GABA described above, ingestion can be carried out upon training. In such as case, ingestion is possible in any of before initiation of training, after initiation and during training. In addition, in one embodiment of the present disclosure, the composition of the present disclosure can be ingested together with food and can be repeatedly ingested on a daily basis. Training is not particularly limited as long as a certain intensity of load is applied for a certain amount of time, including, for example: whole body endurance reinforcing trainings such as interval training, circuit training, walking, jogging, running, LSD (long slow distance), swimming, aquabics, cycling, aerobiking, aerobics, cross-country skiing, STEP exercise and low-oxygen training; muscle reinforcing trainings including self-weight training, free weight training, tube training, machine training, slow training, core training and the like; instantaneous force reinforcing trainings such as plyometric training and ballistic training; agility reinforcing trainings such as sprint training and quickness training; balance (equilibrium) training such as stabilization; flexibility trainings such as stretching and PNG stretching; and the like. In addition, in other embodiments, training can include manual labors and physical activities that apply a certain load or more in daily life in addition to so-called exercise activities including sports, aerobic exercise and anaerobic exercise.

In one embodiment of the present disclosure, the composition of the present disclosure can enhance the effect of improving endurance by a training by being ingested upon the training described above. The composition of the present disclosure is characterized by comprising GABA and is capable of improving endurance by the action of GABA, preferably further enhancing the effect of improving endurance by a training. When a training is continuously carried out, capillaries around a muscle fiber will develop. When a capillary is developed, the amount of blood flowing into a muscle fiber increases and carried oxygen would increase in proportion to the increase of the amount of blood to improve endurance by enlargement of ATP production amount by mitochondria. In one embodiment of the present disclosure, the composition of the present disclosure can further enhance general endurance improvement effect by such a training by the action of GABA.

In one embodiment of the present disclosure, the intensity of a training that enhances the effect of improving endurance by the composition of the present disclosure should be low to moderate intensity or greater such as walking or jogging, preferably may be a training of about 2 METs or greater, about 3 METs or greater, about 4 METs or greater, about 5 METs or greater, about 6 METs or greater, about 7 METs or greater, about 8 METs or greater, about 9 METs or greater, about 10 METs or greater, about 11 METs or greater, about 12 METs or greater, about 13 METs or greater, about 14 METs or greater, or about 15 METs or greater. MET (METs) is an indicator of a training intensity expressed by an oxygen ingestion amount per 1 kg of body weight per unit time, wherein the oxygen ingestion amount upon resting (3.5 mL/kg/minute) is 1 MET, 3 to 6 METs is moderate intensity of exercise, and 7 METs or greater is high intensity of exercise.

For example, walking of 5.6 to 6.4 km/hour for the purpose of exercise is 4.8 METs (National Institute of Health and Nutrition, revised edition of "Shintai katsudou no mettsu (METs) hyou (Table of METs of physical activity)"), wherein when this walking is carried out for 1 hour, the METs would be 4.8. Thus, in one embodiment of the present disclosure, the composition of the present disclosure can enhance the endurance improvement effect by such walking.

In addition, in one embodiment of the present disclosure, the intensity of a training that enhances the effect of improving duration by the composition of the present disclosure can have a total MET count per week that is about 5 METs or greater, about 10 METs or greater, about 15 METs or greater, about 20 METs or greater, about 25 METs or greater, about 30 METs or greater, about 35 METs or greater, about 40 METs or greater, about 45 METs or greater, or about 50 METs or greater. For example, when carrying out a training of 30 METs in one week, it is necessary to carry out a training of 6 METs (e.g., 6.4 km/hour running) (same table) 5 hours per week, wherein said running may be carried out for 1 hour for 5 days, or said running may be carried out for 2 and a half hours twice a week. Alternatively, a running of 8.4 km/hour (9 METs) (same table) may be carried out for 1 hour twice a week and a running of 6.4 km/hour (6 METs) (same table) may be carried out for 1 hour twice a week to achieve a total of 30 METs. In one embodiment of the present disclosure, the composition of the present disclosure can enhance the endurance improvement effect by a training with such a predetermined total MET count or greater.

In addition, in one embodiment of the present disclosure, the intensity of a training that enhances the effect of improving duration by the composition of the present disclosure may have a value obtained by (heart rate/maximum heart rate)×100 that is about 50%, about 55%, about 60%, about 65%, about 70%, about 75%, about 80%, about 85%, about 90%, about 95%, about 100%, or about 100% or greater. For example, when a human with the maximum heart rate of 190 attempts to carry out a training with the intensity of 80%, the training should be carried out so that the heart rate would be 152 (=0.8×190). In other embodiments, a training intensity can also be calculated with {(heart rate−heart rate upon rest)/(maximum heart rate−heart rate upon resting)}×100. In one embodiment of the present disclosure, the composition of the present disclosure can enhance endurance improvement effect by a training with such a predetermined training intensity or greater.

In one embodiment of the present disclosure, the intensity of a training that enhances the effect of improving endurance by the composition of the present disclosure may be, in a case of a muscle reinforcing training, a low load of about 12 to about 30 RM or greater, a moderate load of about 4 to about 12 RM, or a high load of about 1 to 3 RM. RM is an indicator of a training intensity expressed with the maximum lifting weight, wherein a load that enables performance of only 1 time would be 1 RM. In one embodiment of the present disclosure, the composition of the present disclosure can enhance the endurance improvement effect by a training with such a predetermined training intensity or greater.

Herein, "improvement of endurance", regarding a certain exercise or training, refers to extension of continuation time of said exercise or training, or amelioration of performance within a certain time period. For example, in one embodiment of the present disclosure, the effect of improving endurance by the composition of the present disclosure refers to, regarding the above-mentioned 6.4 km/hour running (6 METs), extension of the continuation time thereof compared to before and after ingestion of the composition of the present disclosure, or the concept of being able to carry out, for example, an 8.4 km/hour running (9 METs) within the same time period.

In a preferable embodiment, the composition of the present disclosure may enhance endurance improvement by a training. In other words, compared to the improvement of endurance by continuing a certain exercise or training for a certain time period, the degree of improvement of endurance by continuing a certain exercise or training for a certain time period while ingesting the composition of the present disclosure may be greater. For example, compared to the case in which a 5.6 to 6.4 km/hour walking (4.8 METs·hour) is continued to enable a 6.4 km/hour running (6 METs·hour) within the same time period by the training effect thereof, the composition of the present disclosure may enable a 8.4 km/hour running (9 METs·hour).

Alternatively, in one embodiment of the present disclosure, the effect of improving endurance by the composition of the present disclosure can, regarding a muscle training with the load of 5 RM for example, increase the possible number of lifts thereof, or increase the weight corresponding to 5 RM in the comparison between before and after ingestion of the composition of the present disclosure. In other embodiments, when a weight corresponding to 5 RM is 50 kg for example, compared to when a muscle training of 5 RM is continuously carried out and the weight corresponding to 5 RM became 60 kg by the training effect thereof, the composition of the present disclosure enables training in which the weight corresponding to 5 RM is 70 kg.

Herein, "endurance" refers to the ability of maintaining the above-described exercise or training for a long time, including maintained contraction activity of a muscle, or anti-fatigue action of a muscle. Endurance includes muscle endurance which is the ability of maintaining local muscle exercise for a long time and a whole body endurance which is the ability of maintaining whole body exercise for a long time.

Herein, "muscle endurance" refers to endurance of a skeletal muscle, i.e., the ability of enabling a skeletal muscle to maintain repetition of contraction for a long time, or the ability of maintaining exercise using a part of a skeletal muscle for a long time. For example, improvement of muscle endurance enables a run continued for a long time, or even when intermittent exercise for a short time is repeated, reduction of the exercise performance thereof is suppressed. Furthermore, herein, "whole body endurance" refers to the ability of maintaining whole body exercise using muscles of the entire body including cardiopulmonary function such as heart muscles for a long time.

In one embodiment of the present disclosure, the composition of the present disclosure may be a composition for increasing the amount of glycogen in a skeletal muscle. In addition, in other embodiments, the composition of the present disclosure can be a composition for promoting glycogen loading in a skeletal muscle. Among sports players and athletes, a glycogen loading (carbo loading) method, wherein glucide which is the energy source is saved up in a muscle and liver upon a game or competition in the expectation of improvement of endurance, is known. The glycogen loading method utilizes the fact that glycogen synthase in a muscle or liver with reduced energy source is activated by reducing the amount of glycogen of the muscle or liver by training beforehand and then switching to high glucide meals. Since increase in the amount of glycogen in a muscle is known to improve endurance, the composition of the present disclosure can increase the amount of glycogen in a skeletal muscle, or promote glycogen loading to improve endurance.

When efficiently improving a sports player's endurance by an orally ingested product, doping must be prevented at the same time. Thus, it is desirable to efficiently improve endurance by ingestion of a nutrient utilized as a normal food. In this viewpoint, the GABA of the present invention is preferable as a supplementary orally ingested product for improvement of endurance (especially improvement of endurance by a training).

In addition, also regarding improvement of endurance in daily life, since there may be cases of being ill or already having taken a medicament, it is desirable to efficiently improve endurance by ingestion of a nutrient which is widely distributed in the natural world and can be easily utilized, and not to improve endurance by a non-natural chemical synthetic product or the like. In addition, especially during exercise, or in nutrition supplementation before and after exercise, a product with an unpleasant aftertaste should be avoided. Even in this viewpoint, the GABA of the present invention is preferable as a supplementary orally ingested product for improvement of endurance (especially improvement of endurance by a training).

In one embodiment of the present disclosure, the composition of the present disclosure may be a composition for decreasing the amount of insulin in plasma. When the amount of insulin released in plasma is reduced by the composition of the present disclosure, sensitivity to insulin would increase and insulin resistance would be ameliorated, thereby being able to promote intake of blood sugar in a muscle cell and increase the amount of glycogen. Thus, the composition of the present disclosure can decrease the amount of insulin in plasma and increase the amount of glycogen in a skeletal muscle to improve endurance.

In one embodiment of the present disclosure, the composition of the present disclosure may be a composition for suppressing phosphorylation of protein kinase B (AKT) in a skeletal muscle. It is known that AKT is phosphorylated for activation when insulin is secreted. Since the composition of the present disclosure is a composition that can improve endurance by reducing the amount of insulin in plasma and increasing the amount of glycogen in a skeletal muscle, the composition of the present disclosure can suppress phosphorylation of AKT.

In one embodiment of the present disclosure, the composition of the present disclosure may be a composition for increasing the amount of expression of AMPK protein in a skeletal muscle. AMPK (AMP-activated protein kinase) is known to carry a significant role in energy metabolism regulation. During exercise wherein a skeletal muscle repeatedly contracts, an intracellular AMP/ATP ratio, which is considered as reflecting an intracellular energy state, oxygen state, or stress state, elevates and AMPK is phosphorylated for activation by sensing the above to promote metabolism of sugar and lipid. It is considered that AMPK of a skeletal muscle would be activated by exercise, wherein when AMPK is activated, proliferation of mitochondria, increase of glucose transporter 4 (GLUT4) and increase of type 3 uncoupling protein (UCP3), promotion of phosphorylation of PGC-1α, deacetylation of PGC-1α, or the like would occur to promote metabolism of sugar and lipid. The composition of the present disclosure promotes phosphorylation or activation of AMPK in a skeletal muscle to promote metabolism of sugar and lipid and enable efficient energy supply to enable improvement of endurance.

In one embodiment of the present disclosure, the composition of the present disclosure may be a composition for increasing the amount of expression of PGC-1α protein in a skeletal muscle. PGC-1α (Peroxisome proliferator-activated receptor gamma coactivator 1-alpha) is a transcriptional coactivator that controls energy metabolism in an organism, wherein it is known that PGC-1α localizing in a cytoplasm transfers into a cell nucleus due to activation of AMPK and interacts with various transcription factors to promote biosynthesis of mitochondria, have the action of increasing the amount of expression of glucose transporter GLUT4, or the like. PGC-1α increases its expression in a skeletal muscle by exercise and is related in biosynthesis of mitochondria or increase in the expression of genes associated with energy metabolism, wherein, based on such action of controlling energy production, PGC-1α is known to be involved in promotion of endurance. The composition of the present disclosure can improve endurance by increasing the amount of expression of PGC-1α protein in a skeletal muscle.

A PGC-1α protein is known to be involved in turning a skeletal muscle into slow muscle (Nature August 2002, 418, 797-801), and increase in the amount of expression of PGC-1α protein may lead to enhancement of the amount of slow muscle. Therefore, in one embodiment of the present disclosure, the composition of the present disclosure may be a composition for enhancing the amount of slow muscle in a skeletal muscle. "Enhancement of the amount of slow muscle" refers to increase in the cross-sectional area or the number or proportion thereof of a slow muscle-type muscle fiber in a skeletal muscle, or production of more energy by increase in the number of capillaries in a slow muscle-type muscle fiber in a skeletal muscle. A slow muscle-type muscle fiber contracts at a slow speed to enable continuous exertion of a small force for a long time. Therefore, the composition of the present disclosure enhances the amount of slow muscle to enable improvement of endurance. In addition, herein, "enhancement of a muscle fiber" refers to increase of the cross-sectional area or the number or proportion thereof of type I muscle fiber or type IIa muscle fiber in a skeletal muscle, or production of more energy by increase in the number of capillaries in type I muscle fiber or type IIa muscle fiber in a skeletal muscle.

Muscle fibers are histochemically classified into slow muscle systems and fast muscle systems, and further divided, based on the difference in the myosin heavy chain (MHC) that takes up most of the muscle protein, into four types, which are slow muscle system type I muscle fibers (Type 1, (MHC1)) and fast muscle system type II muscle fibers (Type 2, (MHC2a, MHC2b, MHC2x)), wherein those muscle fibers with different metabolism profiles exist in a mosaic-like manner in many skeletal muscles.

In one embodiment of the present disclosure, the composition of the present disclosure may be a composition for increasing the amount of expression of myosin protein, preferably MHC2a in a skeletal muscle. Myosin is a myofibrillar protein existing in a skeletal muscle, taking up about 50 to 60% of a muscle protein together with actin. Myosin is a hexameric protein consisting of two myosin heavy chains (MHCs) and four myosin light chain subunits. Since a region carrying ATPase activity of myosin exists in an MHC, it is considered that an MHC plays an important part as a motor protein of myosin.

While MHC1 has slow muscle contraction speed compared to MHC2 and has weak exerted isometric tension, it is known that MHC1 has the characteristic of unlikeliness of fatigue in view of the large content of mitochondria and the level of ATP synthesis ability. On the other hand, while MHC2 has fast muscle contraction speed compared to MHC1 and has strong exerted isometric tension, MHC2 has a property such as low ATP synthesis ability. Three isoforms of MHC2 (MHC2a, MHC2x, MHC2b) are known to have characteristic close to the slow muscle-type in the order of 2a>2x>2b, wherein especially 2a is strongly involved in exercise performance. While the proportion of the fiber type of a normal human is 2:1 from 2a:2b+2x, it is known that the proportion of 2a is large in first class athletes regardless of the type of the competition the athlete plays in and type 2b and type 2x hardly exist especially in the fibers of marathon runners or competitive swimmers. In view of the above, it is considered that acceleration of the expression of myosin protein, especially MHC2a, leads to obtainment of enduring ability. The composition of the present disclosure can improve endurance by increasing the amount of expression of myosin protein, preferably myosin heavy chain (MHC) 2a, in a skeletal muscle.

In one embodiment of the present disclosure, the composition of the present disclosure may be a composition for increasing the amount of mitochondrial DNA in a skeletal muscle. Increase in the amount of mitochondrial DNA or activation of mitochondria is considered as having an effect similar to a training, thereby improves endurance. For example, in aerobic exercise, a TCA circuit in mitochondria and an electron transmitting system thereafter causes the ATP produced using oxygen to be supplied and become an energy source, and, in anaerobic exercise, ATP produced from an ATP-CP system or an oxygen-free system such as a lactic acid system is mainly utilized. Thus, the composition of the present disclosure can improve endurance by increasing the amount of mitochondrial DNA in a skeletal muscle.

In one embodiment of the present disclosure, the content of GABA in the composition of the present disclosure is not particularly limited as long as the concentration or weight is enough to achieve the effect of the composition of the present disclosure in accordance with the method of administration thereof or the like. The content of GABA in the composition of the present disclosure is preferably about 10 to about 2000 mg, wherein the lower limit of the content may be, for example, about 10 mg or greater, about 30 mg or greater, about 50 mg or greater, about 70 mg or greater, about 100 mg or greater, about 150 mg or greater, about 200 mg or greater, about 300 mg or greater, about 400 mg or greater, about 500 mg or greater, or about 700 mg or greater, and the upper limit of the content may be, for example, about 2000 mg or lower, about 1800 mg or lower, about 1500 mg or lower, about 1300 mg or lower, about 1000 mg or lower, about 800 mg or lower, about 700 mg or lower, about 600 mg or lower, or about 500 mg or lower. The content may be any range of numerical values between these lower limits and upper limits.

In one embodiment of the present disclosure, the composition of the present disclosure can comprise any additive or any component that can be used for a composition that can be ingested in a body other than GABA in accordance with the form thereof. Examples of these additives and components include, but are not limited to, vitamins including vitamin E and vitamin C, minerals, nutrient components, bioactive components such as aromatics, excipients mixed upon preparation, binders, emulsifiers, tensioning agents (isotonicifier), buffers, dissolution assisting agents, antiseptic agents, stabilizers, antioxidants, coloring agents, coagulants, or coating agents and the like.

In one embodiment of the present disclosure, the form of the composition of the present disclosure is not particularly limited as long as the composition includes GABA, wherein the composition can be, for example, a pharmaceutical composition, drinking/eating product (including food for specified health, nutrition function food, functional food such as food with a functional claim, health assistant food, health food, supplement and the like), food additive, quasi-drug, or medicament.

In one embodiment of the present disclosure, the composition of the present disclosure can be orally ingested wherein when used as an oral agent, the form thereof can be, for example, a tablet (including coated tablet), capsule, powder agent, granular agent, powdered agent, liquid agent, suspension, emulsion, particle-like agent, powder agent, round agent, paste-like agent, cream-like agent, couplet-like agent, gel-like agent, chewable agent, stick-like agent, or the like. In addition, the composition can be used as a raw material of other medicaments after being regulated to a form that can easily be mixed such as powder form or granule form.

In one embodiment of the present disclosure, the composition of the present disclosure can be used for non-therapeutic usage, wherein it is possible to arrive at a non-therapeutic method of improving endurance by ingesting the composition of the present disclosure. Such a method does not include therapeutic actions or medical actions and the target thereof is not particularly limited. It is possible to achieve the effect of improving endurance against sports players who carry out trainings on a daily basis and also healthy people who normally do not carry out exercise often by ingesting the composition of the present disclosure. In addition, when used as a medicament or quasi-drug, it is possible to solicit the efficacy of improvement of endurance or the like.

In one embodiment of the present disclosure, the amount of ingestion per day of the GABA comprised in the composition of the present disclosure can be appropriately regulated based on the form of the composition, method of ingestion, purpose of use and the ingestion target's age, weight, symptom and the like. For example, from the viewpoint of more significantly exerting the effect of GABA comprised in the composition of the present disclosure, the amount of ingestion per day of the GABA comprised in the composition of the present disclosure preferably can be the ingestion that would achieve about 10 mg/day or greater, more preferably can be the ingestion that achieves about 25 mg/day or greater, about 50 mg/day or greater, about 60 mg/day or greater, about 80 mg/day or greater, about 100 mg/day or greater, about 120 mg/day or greater, about 150 mg/day or greater, about 180 mg/day or greater, about 200 mg/day or greater, about 300 mg/day or greater, about 400 mg/day or greater, about 500 mg/day or greater, about 800 mg/day or greater, about 1000 mg/day or greater, about 1200 mg/day or greater, about 1500 mg/day or greater, about 1800 mg/day or greater, or about 2000 mg/day or greater. The upper limit of the amount of ingestion per day of the GABA comprised in the composition of the present disclosure is not particularly limited as long as the amount is in the range in which the composition of the present disclosure can exert the effect of improving endurance.

In one embodiment of the present disclosure, the frequency of application of the method of the present disclosure, or the frequency of ingestion of the composition of the present disclosure may be once or divided into multiple times in one day within the range of the desired amount of ingestion. In addition, the ingestion period can be appropriately set in the range in which the composition of the present disclosure can exert the effect of improving endurance.

Herein, "about" refers to ±10% of the numerical value that follows.

EXAMPLES

While the present disclosure is explained in more details below using Examples, the present disclosure is not limited to these Examples.

The experimentation methods and materials used in the present disclosure are explained below. While the present embodiment uses the following experimentation method, the same result can be obtained by using other experimentation methods.

Example 1

Examination of the Effect of Improving Endurance by GABA

Repetition of a training that applies high load improves physical function. In this regard, the following test is carried out to confirm the effect of GABA ingestion against the effect of improving endurance by a training.
(Group of Mice for Running Test)
Mice used for measurement of limit running time using a treadmill are divided into four groups as shown in Table 1 below.

TABLE 1

|  |  | 0.5% GABA ingestion (0.8 g for human) | |
| --- | --- | --- | --- |
|  |  | No | Yes |
| Training | No | Control group . . . (1) | GABA group . . . (2) |
|  | Yes | Training group . . . (3) | GABA training group . . . (4) |

Specifically, 10 week-old male ICR mice are classified into the group in which normal food is freely ingested and training is not carried out (control group), the group in which a diet of normal food added with 0.5% of GABA (1.8 g for human) is freely ingested and training is not carried out (GABA group), the group in which normal food is freely ingested and training is carried out (training group) and the group in which a diet of normal food added with 0.5% of GABA (1.8 g for human) is freely ingested and training is carried out (GABA training group) (9 mice in each group).
(Training Using a Treadmill)

During the test period, the above classified mice freely ingested about 2.7 to about 5.0 g/day of normal food or GABA-comprising food per one individual. Regarding the training group and the GABA training group, running was forced for 60 minutes on a schedule of 3 times a week (interval of 1 day or 2 days). This training was continued until 3 days after termination of the below-mentioned third running test. In the training, a treadmill for small animals (Meiquest Ltd.) was used with the gradient of 0 degree to force running at 25 m/minute running speed. Since a mouse will run at the speed of about 6 to 24 m/minute without a load, the running speed of 25 m/minute is a little faster than normal, i.e., low to moderate intensity.
(Measurement of Limit Running Time Using a Treadmill)

Figure 2:
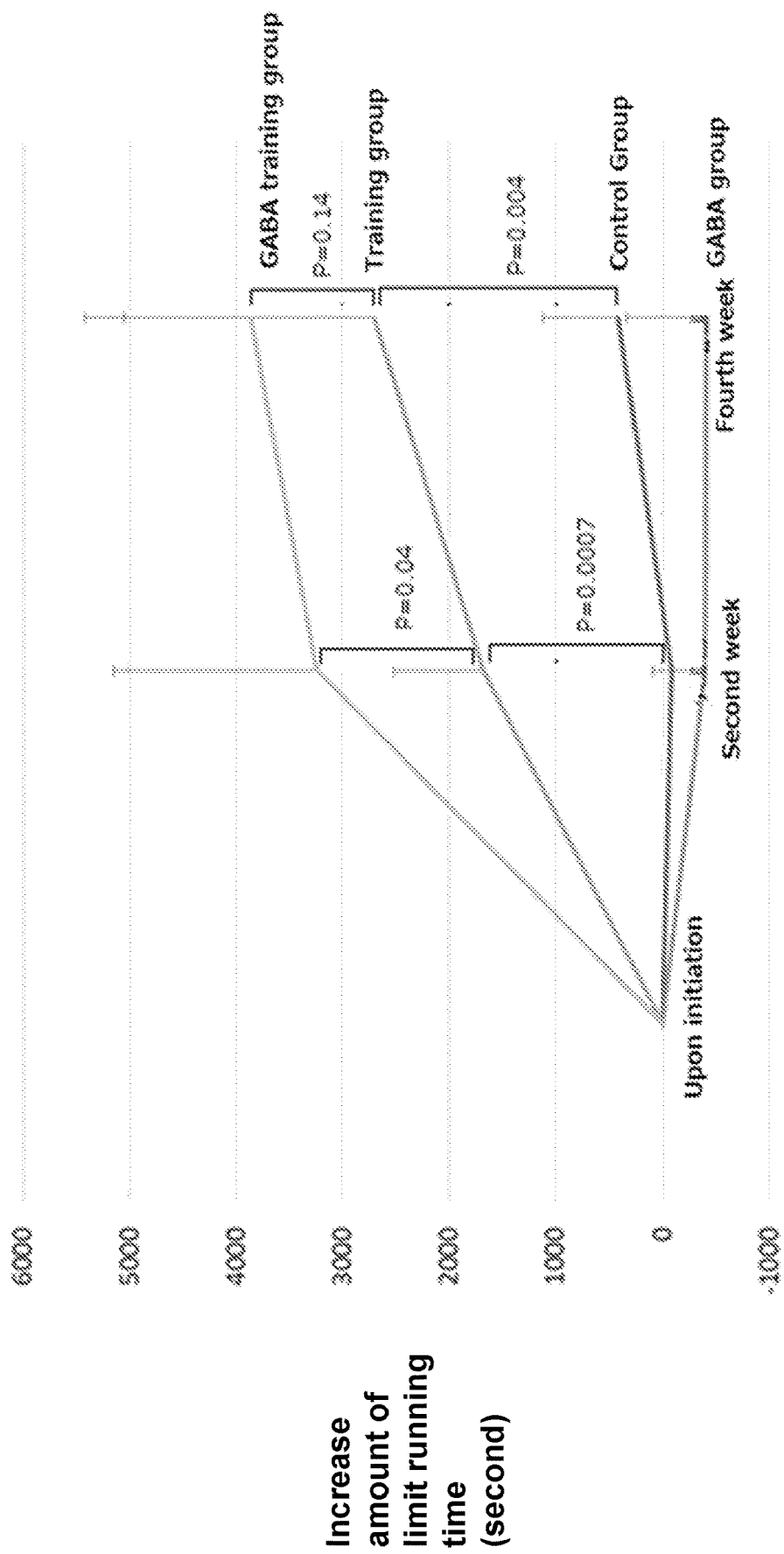
FIG. 2 is a graph showing a result of measurement of limit running time of one embodiment of the present disclosure.

Four groups of mice prepared in the above-described manner were used to measure the limit running time using a treadmill for small animals (Meiquest Ltd.). The running test has a mouse run on a treadmill with the gradient of 5 degrees to measure the time it takes for the mouse to become exhausted and not run anymore. Regarding the running speed, a mouse had to run at 15 m/minute for 5 minutes at first, then an increase by 2 m/minute is made every 2 minutes, and the speed was gradually increased up to 30 m/minute. After reaching 30 m/minute, the running speed was fixed to continue the running test. The running test was carried out a total of 3 times, which are at the time of the initiation of the test, after 2 weeks, and after 4 weeks using the schedule shown in FIG. 1. When a mouse failed to run by itself for 3 seconds or longer and continuously crashes into the wall of the treadmill behind 5 times, it is determined that the mouse is in a state of no longer being able to run. FIG. 2 shows the result of measurement of the running time that it takes to reach exhaustion at the time of initiation of the test (first time), after two weeks (second time) and after four weeks (third time).

Since both the GABA training group and the training group continued training to increase the running time that it takes to reach exhaustion in the running test, it has been shown that endurance is improved by a training. The amount of increase of running time due to a training was significantly enlarged or found to have the tendency to be enlarged in the GABA training group more than the training group (P=0.04 in the second week and P=0.14 in the fourth week). Based on this result, it is understood that GABA enhances the endurance improvement effect by a training.

Example 2

(Measurement of the Amount of Glycogen in a Skeletal Muscle)

2 days after termination of the final training, a gastrocnemius muscle (skeletal muscle) of a mouse of each group is collected to measure the amount of glycogen in a skeletal muscle. The measurement of the amount of glycogen in a skeletal muscle is carried out as described below using a Glycogen Colorimetric/Fluorometric Assay Kit (Bio Vision, Inc.)

10 mg or more of a gastrocnemius muscle of a mouse was taken out to a 1.5 mL plastic tube, to which 20 times as much distilled water was added to carry out homogenization. This was boiled for 10 minutes in hot water. Next, centrifugal separation was carried out for 10 minutes at 18000 g. A 50 µL sample was respectively put in a 96 well plate and 2 µL of hydrolase mix was respectively added to then be stirred. This solution was settled for 30 minutes at room temperature (20 to 25° C.). A mixed liquid for reaction was prepared with the following proportions, wherein 50 µL of this mixed liquid for the reaction was respectively added.

Proportion of mixed liquid for reaction (50 µL)
Development buffer 46 µL
Development enzyme mix 2 µL
OxiRed probe 2 µL A solution added with the mixed liquid for reaction was shaded at room temperature and settled for 30 minutes. Absorbance was measured (OD 570 nm) to calculate the amount of glycogen in a skeletal muscle.

Figure 3:
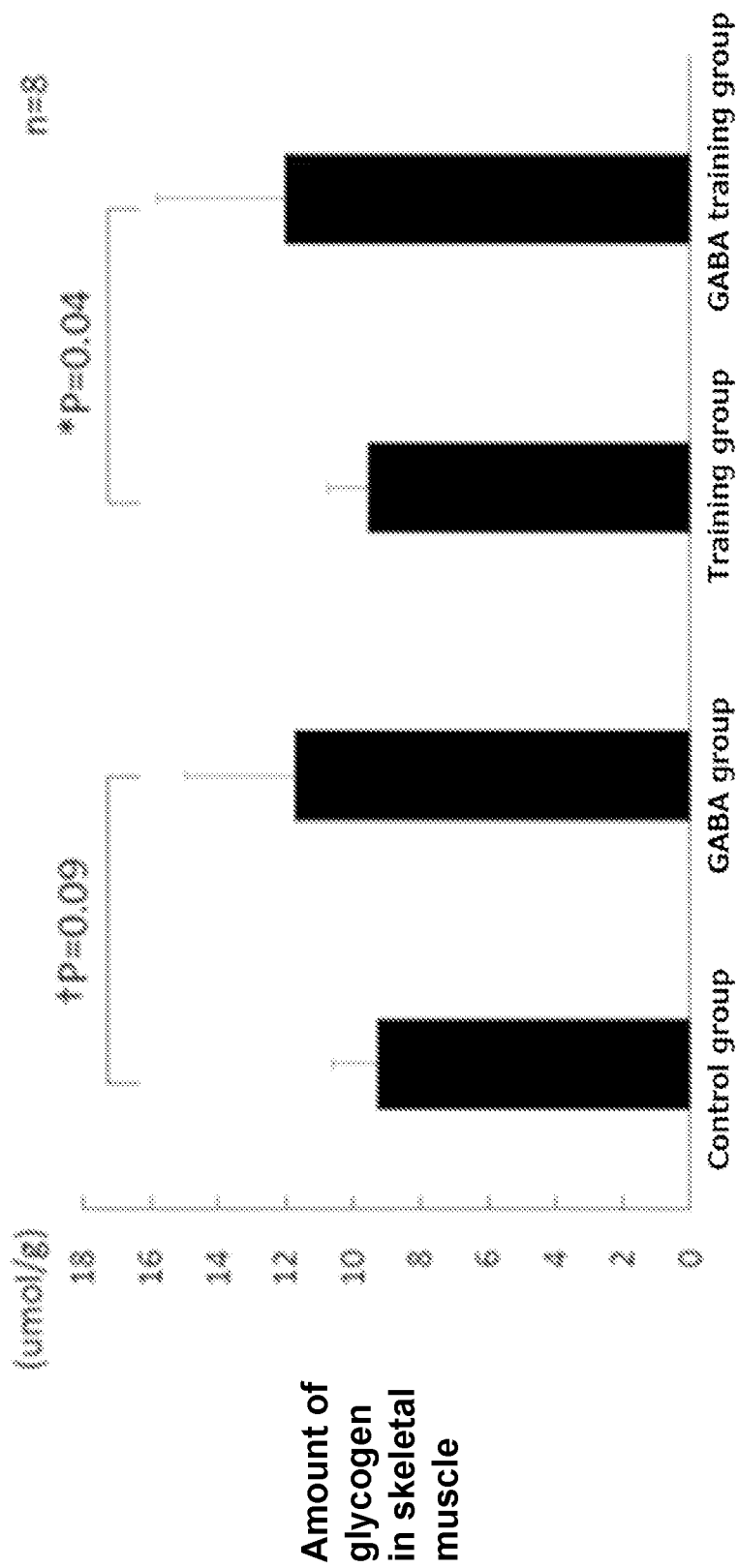
FIG. 3 is a graph showing a result of measurement of the amount of glycogen in a skeletal muscle of one embodiment of the present disclosure.

FIG. 3 shows the result of the measurement of the amount of glycogen in the manner described above. Compared to the control group, tendency of increase has been found regarding the amount of glycogen in the gastrocnemius muscle of the GABA group (P=0.09). Furthermore, in the GABA training group, the amount of glycogen in the gastrocnemius muscle was significantly increased more than the training group (P=0.04). Based on the above result, it is shown that GABA increases the amount of glycogen in a skeletal muscle. In addition, it is shown that, even when carrying out a training, the amount of glycogen in a skeletal muscle is increased by ingestion of GABA together with the training.

Example 3

(Measurement of the Amount of Insulin in Plasma)

2 days after termination of the final training, blood of a mouse in a group is collected to measure the amount of insulin in plasma. The measurement of the amount of insulin in plasma was carried out as described below using Lbis (registered trademark) Insulin-Mouse T (FUJIFILM Wako Shibayagi Corporation).

96 well plate for turning an antibody into a solid phase was prepared and washed 4 times with a cleaning liquid. 100 µL of biotin binding anti-insulin antibody was added thereto and stirred. 10 µL of each group's mouse's serum sample or standard insulin solution was respectively added thereto, stirred and settled for 2 hours at room temperature (20° C. to 25° C.). The 96 well plate was washed 4 times with a washing liquid, 100 µL of peroxidase-avidin binding product was respectively added, stirred and settled for 30 minutes at room temperature (20° C. to 25° C.). 100 µL of tetramethylbenzidine solution was respectively added and the 96 well plate was washed 4 times with a washing liquid. 100 µL of 1M sulphuric acid solution was respectively added to stop the reaction, measure absorbance (OD 450 nm) and calculate the amount of insulin in plasma.

Figure 4:
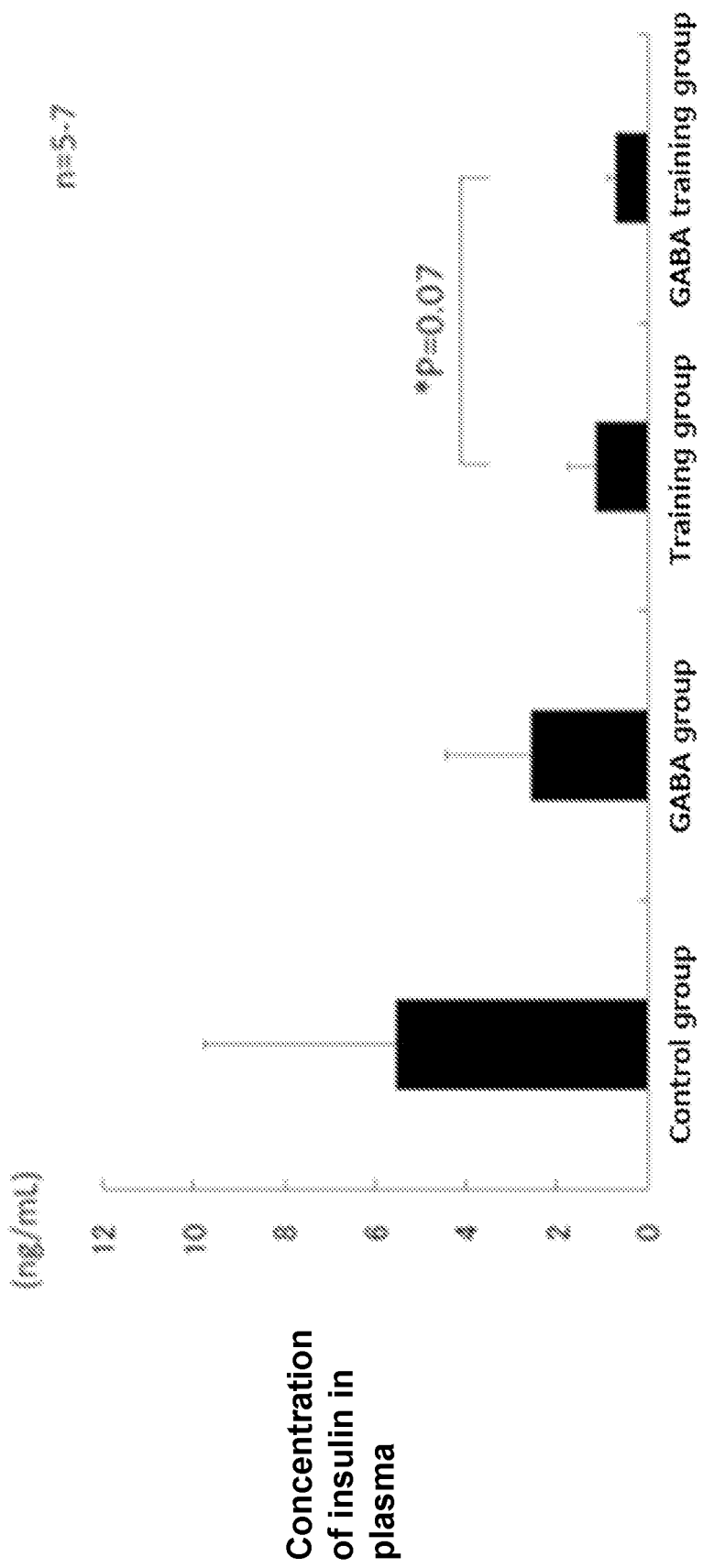
FIG. 4 is a graph showing a result of measurement of the amount of insulin in plasma of one embodiment of the present disclosure.

FIG. 4 shows the result of measurement of the amount of insulin in the manner described above. Compared to the control group, the amount of insulin decreased in all of the GABA group, training group and GABA training group. Alternatively, even when comparing the training group and the GABA training group, the amount of insulin decreased in the GABA training group (P=0.07). Based on the above result, it is shown that the GABA or training decreases the amount of insulin in plasma, wherein especially GABA further enhances the effect of decreasing the amount of insulin by a training.

Example 4

(Measurement of the Amount of Relative Expression of PGC1α and AMPK Protein in a Skeletal Muscle)
{Western Blotting Method}
(Preparation of Tissue Sample)

Two days after termination of the final training, a gastrocnemius muscle (skeletal muscle) of a mouse of each group was collected. A tissue fragment of the gastrocnemius muscle was taken out to a 1.5 mL plastic tube for measurement. RIPA Buffer (NACALAI TESQUE, INC.) that is 3 times the amount of the weight of the tissue fragment was added, homogenization was carried out and centrifugal separation of 18000 g×20 was carried out. The amount of protein was quantified in accordance with the method of the TaKaRa BCA Protein Assay Kit (TAKARA BIO INC.) using bovine serum albumin as a standard protein. The protein concentration was prepared with a RIPA buffer and the concentration was unified to 50 µg/ml. A 2×4×SDS sample buffer (150 mM Tris-HCl, pH7.0, 12% sodium dodecyl sulfate, 25% glycerol, 0.02% bromophenol blue, 5% 2-mercaptoethanol) in the amount that is one fourth of the extraction solution was added and heated for 3 minutes at 98° C. to form a sample for electrophoresis.

(SDS Polyacrylamide Gel Electrophoresis (SDS-PAGE))

SDS-PAGE was carried out in accordance with the method of Laemmli. A separation gel was set to be 5 to 20%, a concentration gel was set to be 5% and 25 mM tris, 192 mM glycine and 0.1% SDS formed an electrophoretic buffer solution. Precision Plus Protein™ Dual Color Standards (Biorad) was used as a marker of molecular weight. Upon phoresis, 20 mA of current was applied for one wide gel.

(Western Blotting Method)

After termination of SDS-PAGE, 20% ethanol was used for shaking and soaking for 5 minutes. iBlot dry blotting system (Thermo Fisher) was used for transcription of protein. After the transfer, a PVDF membrane is blocked for 1 hour with PBS-T (FUJIFILM Wako Pure Chemical Corporation) comprising 0.1% BSA. Dilution was carried out using a primary antibody (rabbit anti-PGC1α antibody (NovusBiologicals), rabbit anti-AMPK (Cell Signaling Technology)) and antigen antibody reaction was carried out in one night in an incubator at 4° C. Then, washing was carried out for 5 minutes 4 times with PBS-T, an HRP label secondary antibody binding to respective primary antibody was diluted with PBS-T for reaction for 1 hour. Then, the PVDF membrane was washed for 5 minutes 4 times for coloring using ECLPrime Western Blotting Detection Reagent (GE Healthcare) to carry out detection with WSE-6100 LuminoGraph I (ATTO CORPORATION). The PVDF film underwent stripping processing with a westernblot striping buffer and dilution was carried out with the primary antibody (GAPDH, monoclonal antibody, peroxidase bond) to carry out antigen antibody reaction for 2 hours. Then, the PVDF membrane was washed for 3 minutes 3 times with TBS (−) for coloring using ECLPrime Western Blotting Detection Reagent to carry out detection with WSE-6100 Lumino Graph I. ImageJ (Nat Methods Jul. 2012 9, 671-675) was used to carry out image analysis and measure the amount of relative expression of GAPDH and target protein.

{Result}

Figure 5:
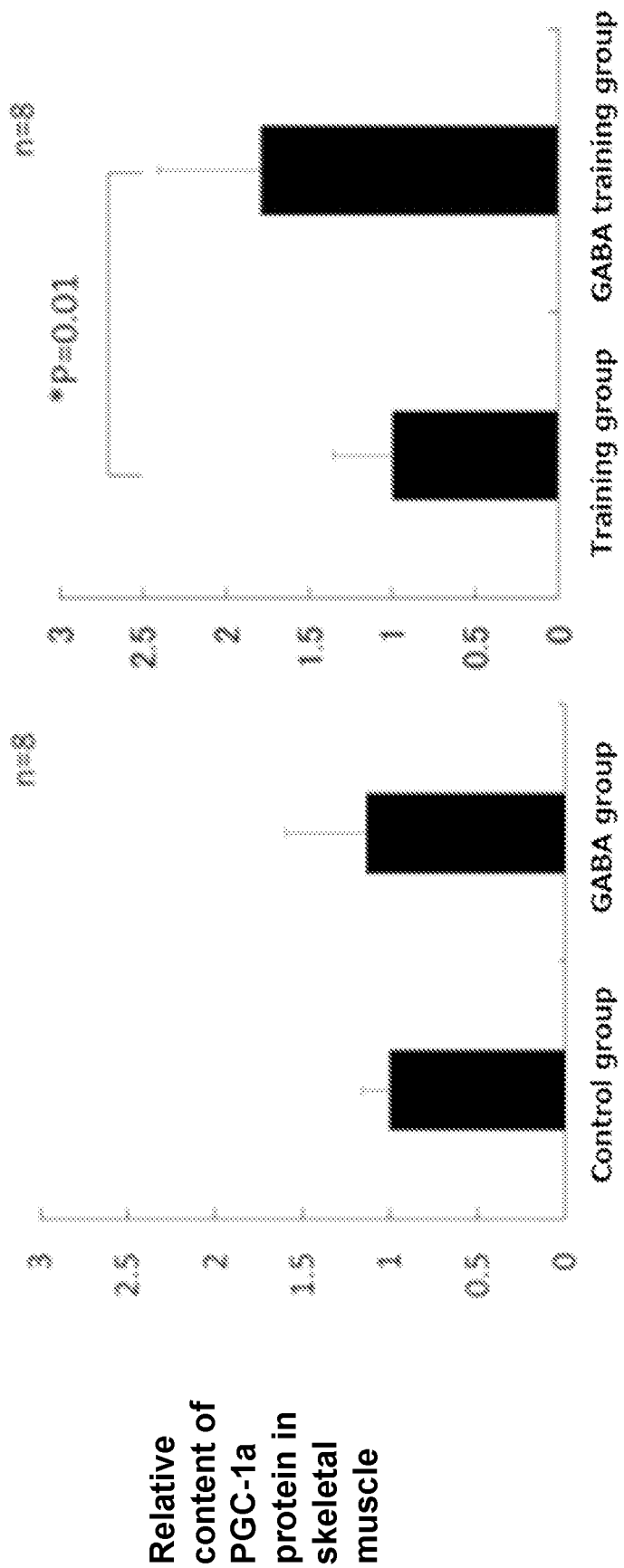
FIG. 5 is a graph showing a result of measurement of the amount of relative expression of PGC-1α protein in a skeletal muscle of one embodiment of the present disclosure.
Figure 6:
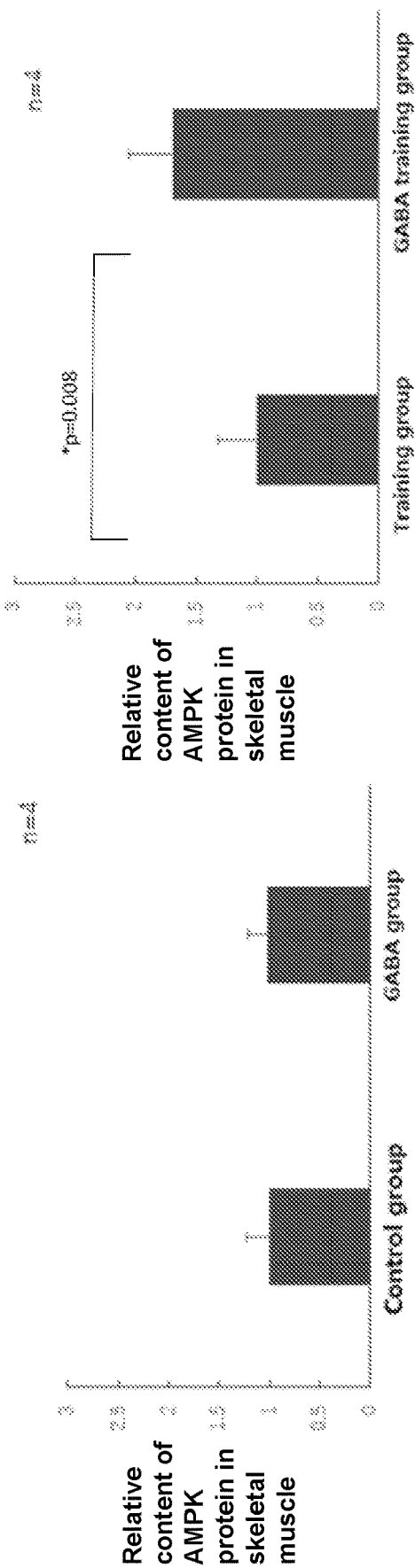
FIG. 6 is a graph showing a result of measurement of the amount of relative expression of AMPK protein of one embodiment of the present disclosure.

FIG. 5 shows the result of measurement of the amount of relative expression of PGC-1α protein and FIG. 6 shows the result of measurement of the amount of relative expression of AMPK protein, in the manner described above. Compared to the control group, the amount of expression of PGC-1α protein in a skeletal muscle was found to have the tendency of increase. Furthermore, in the GABA training group, the amount of expression of PGC-1α protein in a skeletal muscle was significantly increased more than the training group (P=0.01). Based on the above result, it is shown that GABA increases the amount of expression of PGC-1α protein in a skeletal muscle. In addition, it is shown that, even when carrying out a training, the amount of expression of PGC-1α protein in a skeletal muscle is increased by ingestion of GABA together with a training. Based on this result, it is also suggested that a skeletal muscle is promoted to be turned into a slow muscle by ingestion of GABA.

In addition, compared to the control group, the amount of expression of AMPK protein of the training group and the GABA training group increased (P=0.008 and P=0.0008, respectively). Furthermore, in the GABA training group, the expression of AMPK protein increased more than the training group. Based on the above result, it is shown that GABA further enhances the increase of the amount of expression of AMPK protein by a training by ingestion together with a training.

Example 5

(Phosphorylated AKT/AKT Ratio in a Skeletal Muscle)

Three days after termination of the third running test, each group's mouse's gastrocnemius muscle (skeletal muscle) is collected and the amount of expression of phosphorylated AKT and AKT in a skeletal muscle was measured in the same film using the same method as the above-mentioned {western blotting method} to calculate the ratio of the amount of expression of phosphorylated AKT and AKT.

Figure 7:
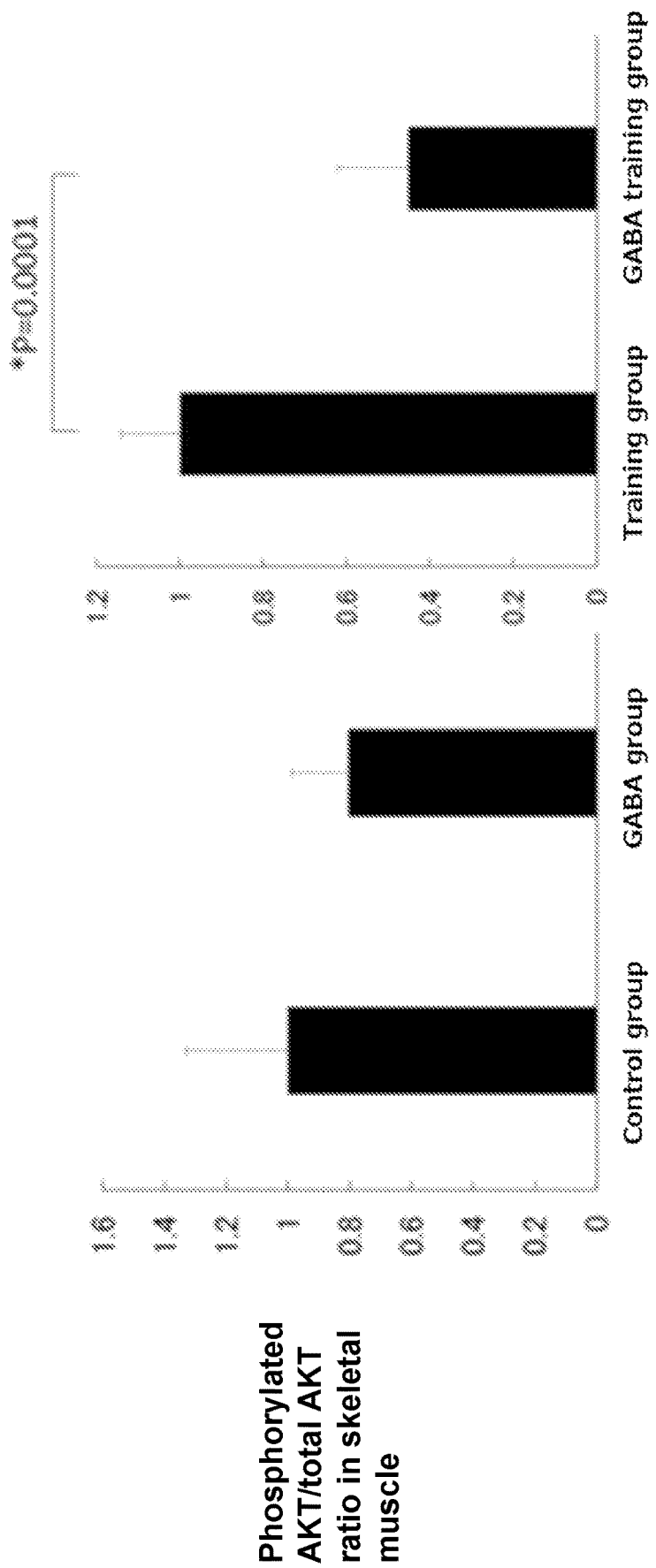
FIG. 7 is a graph showing phosphorylated AKT/AKT ratio in a skeletal muscle of one embodiment of the present disclosure.

FIG. 7 shows the result of measurement of phosphorylated AKT and AKT insulin amount in the manner described above. Compared to the control group, the phosphorylated AKT/total AKT ratio in a skeletal muscle of the GABA group was found to have the tendency to decrease. Furthermore, in the GABA training group, the phosphorylated AKT/total AKT ratio was significantly decreased more than the training group (P=0.0001). Based on the above result, it is shown that GABA decreases the amount of phosphorylated AKT in a skeletal muscle. In addition, it is shown that, even when a training is carried out, the amount of phosphorylated AKT in a skeletal muscle is decreased by ingestion of GABA together with a training.

Example 6

(Measurement of the Amount of Mitochondrial DNA)

20 to 50 mg of tissue sample was taken out to a 2 mL plastic tube to extract DNA in accordance with the genome DNA purification protocol described in NucleoSpin® DNARapidLyse (TAKARA BIO INC.). The amount of relative expression of the amount of mitochondria with respect to mouse nuclear DNA was quantified with the real-time PCR method using Thermal Cycler Dice® Real TimeSystem II (TAKARA BIO INC.) and set as mitochondrial DNA amount.

Figure 8:
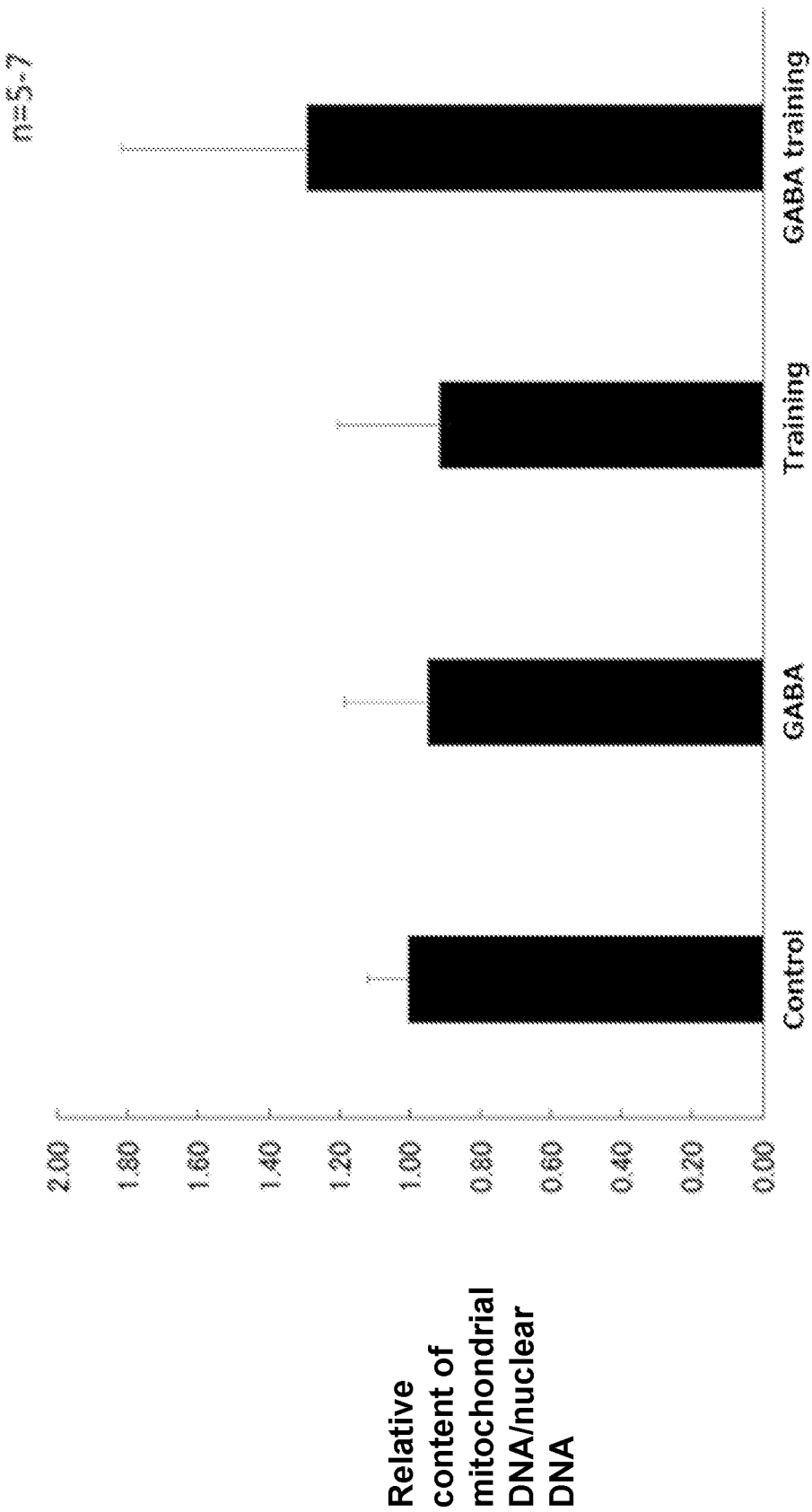
FIG. 8 is a graph showing a result of measurement of the amount of mitochondrial DNA in a skeletal muscle of one embodiment of the present disclosure.

FIG. 8 shows the result of measurement of the mitochondrial DNA amount in a skeletal muscle in the manner described above. Compared to the control group, GABA group and training group, the mitochondrial DNA amount in a skeletal muscle of the GABA training group was found to have the tendency of increase. Based on the above result, it is shown that GABA increases the amount of the mitochondrial DNA amount in a skeletal muscle by ingestion together with a training.

Example 7

(Measurement of the Amount of Relative Expression of Myosin 2a in a Skeletal Muscle (Soleus Muscle))
{Myosin Western Blotting}
(SDS Polyacrylamide Gel Electrophoresis (SDS-PAGE) of Measurement of Myosin)

Two days after termination of the final training, a skeletal muscle (soleus muscle) tissue of mouse was grinded with a biomasher on ice. The grinded soleus muscle tissue was dissolved in 1 ml of a RIPA buffer to prepare a protein extraction liquid. The protein concentration of the protein extraction liquid was measured with a protein assay BCA kit and dilution was carried out with a RIPA buffer so that the protein concentration of the protein extraction liquid would be 4 mg/ml. Dilution was carried out with 4×sample buffer and RIPA buffer so that the final concentration of the protein extraction liquid would be 1 mg/ml and the final concentration of mercaptoethanol would be 5%. This diluent was heated with a block heater under the condition of 10 minutes at 60° C. to form a measurement sample.

Next, 5 mL of phoresis gel made as in the following table was put in a glass plate (10 cm×12 cm) in which two glasses are layered.

TABLE 2

| *Phoresis gel stock | final concentration | 10 ml (for one) |
|---|---|---|
| Glycerol | 30% | 3 ml |
| 30% acrylamide/bis (50:1) | 8% | 2.667 ml |
| 1.5M Tris-HCl (pH 8.8) | 0.2M | 1.333 ml |
| 1M glycine | 0.1M | 1 ml |
| 10% SDS | 0.40% | 0.4 ml |
| 10% APS | 0.10% | 0.1 ml |
| TEMED | 0.05% | 0.005 ml |
| dH2O | | 1.495 ml |
| Total | | 10 ml |

About 1 ml of MilliQ water was layered and left until the gel solidified.

Next, a concentration gel was made as in the following table.

TABLE 4

| *Phoresis gel stock | final concentration | 10 ml (for one) |
|---|---|---|
| Glycerol | 30% | 1.5 ml |
| 30% acrylamide/bis (50:1) | 4 | 0.667 ml |
| 0.5M Tris-HCl (pH 6.8) | 0.07M | 0.7 ml |
| 100 mM EDTA | 4 mM | 0.2 ml |
| 10% SDS | 0.40% | 0.2 ml |
| 10% APS | 0.10% | 0.05 ml |
| TEMED | 0.05% | 0.0025 ml |
| dH2O | | 1.681 ml |
| Total | | 5 ml |

After the water has been thrown out and moisture has been wiped off with a Kimwipe, 2 mL of concentration gel is put in, a comb is inserted and left until the gel is solidified.

Next, a phoresis buffer was prepared as in the following table.

TABLE 3

| | final concentration | 1 L | |
|---|---|---|---|
| *Phoresis buffer 1 | | | |
| Tris (wako) | 0.1M | 12.114 | g |
| Glycine | 150 mM | 11.2605 | g |
| SDS | 0.10% | 1 | g |
| dH2O | | 1 | L Diluting in measuring cylinder |
| *Phoresis buffer 2 | | | |
| Tris (wako) | 0.05M | 6.057 | g |
| Glycine | 0.075M | 5.63025 | g |
| SDS | 0.05% | 0.5 | g |
| dH2O | | 1 | L Diluting in measuring cylinder |

Phoresis buffer 1 was put in the positive-electrode side of an electrophoresis tank, a gel was set, the foam of the bottom of the gel was forced out, phoresis buffer 2 was put in a phoresis apparatus of the electrophoresis tank, and the comb was removed. Glycerol of the well for sample application was forced out by pipetting and a molecular weight marker (Biorad) (2 uL) and 3 uL of sample was applied to the well. Phoresis was carried out for 24 hours with the constant voltage of 70V at 4° C.

A blocking liquid (1% BSA/PBS) was prepared during phoresis and the gel was cut out for shaking for 5 minutes minutes with 20% EtOH. iBlot2 was used and gel was set in accordance with the protocol of iBlot for transcription to a PVDF film. The standard protocol was set to be P0.

The film after transcription was shaken (22° C. (room temperature), 1 hour) with a blocking liquid and the film was shaken for 5 minutes with PBS/0.05% tween20 (PBS-T). The blocking liquid underwent 10-fold dilution with PBS-T to make a diluent of a primary antibody and the primary antibody (anti-mouse myosin IIa antibody (RandDSystems. inc)) was diluted (see the data sheet of the antibody for the dilution rate). The film was put in a nylon bag, three sites were sealed by heat sealing and the primary antibody diluent was put in (about 8 mL). Foam was taken out from the nylon bag, the fourth site was sealed, and primary antibody reaction was carried out for 1 hour at 22° C. (room temperature), or in one night at 4° C. Next, removal from the film is carried out for placement in a container with an appropriate size to wash the film with PBS-T 5 minutes×4 times. Next, as secondary antibody reaction, a secondary antibody diluent was made (about 1/3000) and reacted for 1 hour at 22° C. (room temperature). After the reaction, the membrane was washed with PBS-T 5 minutes×5 times and the coloring substrate was returned to be at room temperature. After being returned to room temperature, a substrate liquid was prepared.

The film was placed on a rap, excess PBS-T was removed with a Kimwipe and the substrate liquid was poured (about 1 mL). Excess substrate liquid was removed with a Kimwipe, inserted between nylons and heat-sealed to then be put in a detection device.

Figure 9:
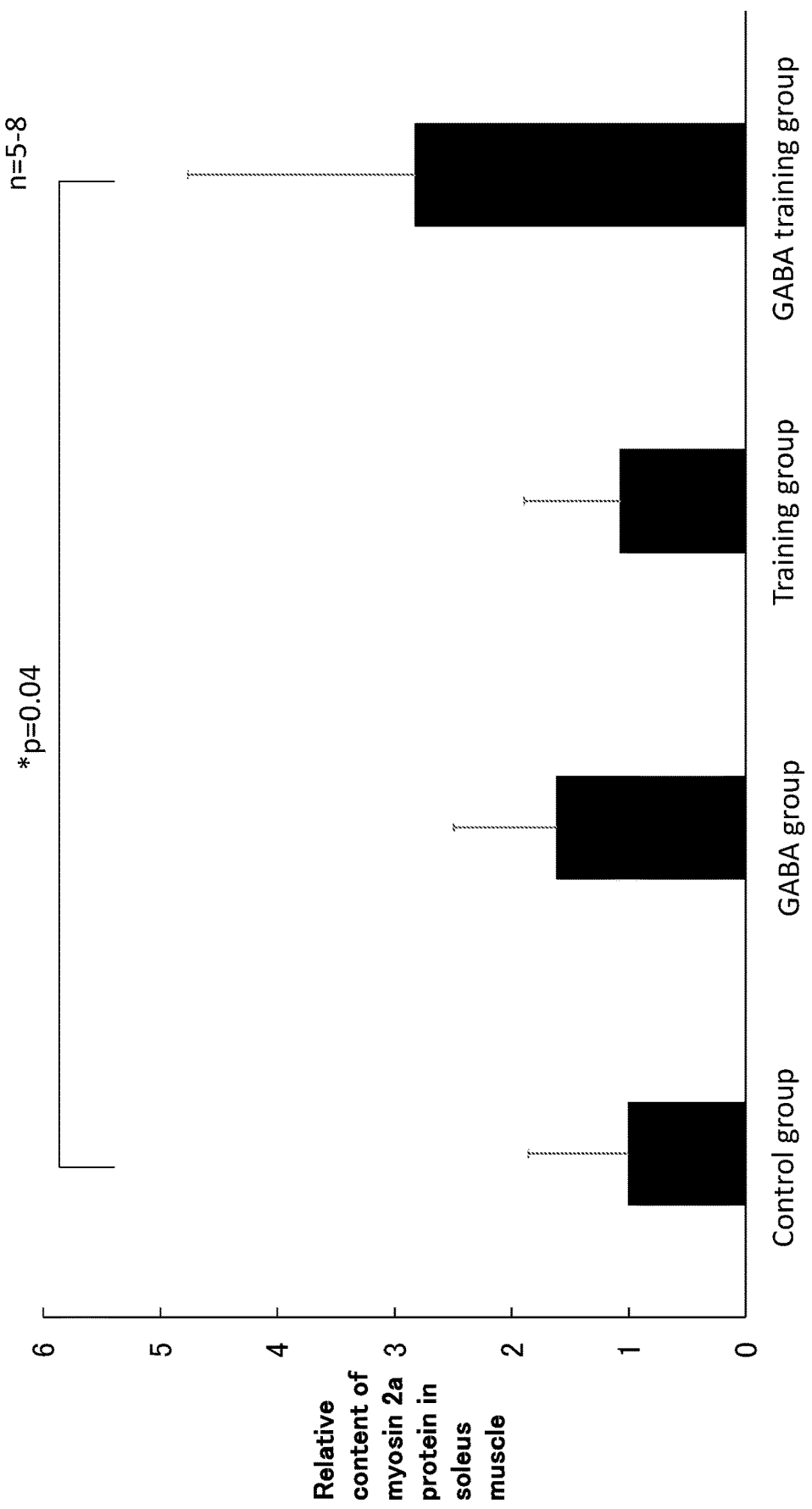
FIG. 9 is a graph showing a result of measurement of the amount of relative expression of myosin 2a protein in a skeletal muscle (soleus muscle) of one embodiment of the present disclosure.

FIG. 9 shows the result of measurement of the amount of relative expression of myosin 2a protein in a skeletal muscle (soleus muscle) in the manner described above. Compared to the control group and the training group, the amount of expression of myosin 2a protein was found to have the tendency to increase in the GABA group. In addition, in the GABA training group, the amount of expression of myosin 2a protein was significantly increased compared to the other 3 groups, wherein obtainment of the synergistic effect of GABA ingestion and training can be understood. Based on the above result, it is shown that GABA increases the amount of relative expression of myosin 2a protein in a skeletal muscle (soleus muscle) by ingestion together with a training.

While the present disclosure has been exemplified using preferable embodiments of the present disclosure as described above, it is understood that the scope of the present disclosure should be interpreted only by the Claims. Any patent, patent application and other documents cited herein should be incorporated herein by reference in the same manner as the contents are specifically described herein. The present application claims priority to the Japanese Patent Application No. 2020-28755 filed on Feb. 21, 2020 before the Japan Patent Office, the content of which being incorporated as a reference in the same manner as if the entirety thereof configuring the content of the content of the present application.

The invention claimed is:

1. A method of increasing slow muscle development in a subject, the method comprising:
    administering an effective amount of γ-aminobutyric acid (GABA) to the subject via daily ingestion for correspondingly increasing slow muscle development in the subject while the subject is in a physically active state defined as engaging in one or more physical activities relative to a physically inactive state defined as the subject being substantially idle, wherein:
    daily administration of the effective amount of GABA over a test period of two consecutive weeks results in an approximate two-fold increase in aerobic performance at an end of the test period, compared to non-administration of the effective amount of GABA over the test period of two consecutive weeks,
    wherein one or more physical activities comprises walking, jogging, running, or manual labors and physical activities in daily life,
    wherein an intensity of the one or more physical activities is 3 to 6 METs, and
    wherein completion of administering the effective amount of GABA results in an increase in an amount of expression of PGC-1α in a skeletal muscle, and the increase of the amount of expression of PGC-1α leads to enhancement of the amount of the slow muscle.

2. The method of claim 1, wherein the effective amount of GABA is about 10 mg or more.

3. The method of claim 1, wherein the effective amount of the GABA is about 10 to about 2000 mg per day.

4. The method of claim 1, wherein GABA is administered orally.

5. The method of claim 1, wherein GABA is administered before initiation of one or more physical activities, during one or more physical activities, or after termination one or more physical activities.

6. The method of claim 5, wherein GABA is administered to increase endurance responsive to participation in one or more physical activities.

7. The method of claim 1, wherein completion of administering the effective amount of GABA results in an increase in muscle endurance of the subject in the physically active state when measured relative to the subject in the physically inactive state.

8. The method of claim 1, wherein completion of administering the effective amount of GABA results in an increase in an amount of glycogen, and/or promoting glycogen loading in a skeletal muscle of the subject in the physically active state when measured relative to the subject in the physically inactive state.

9. The method of claim 1, wherein completion of administering the effective amount of GABA results in a reduction in an amount of insulin in plasma of the subject in the physically active state when measured relative to the subject in the physically inactive state.

10. The method of claim 1, wherein completion of administering the effective amount of GABA results in suppression of phosphorylation of protein kinase B (Akt) in a skeletal muscle of the subject in the physically active state when measured relative to the subject in the physically inactive state.

11. The method of claim 1, wherein completion of administering the effective amount of GABA results in an increase an amount of expression of AMPK protein, and/or myosin protein in a skeletal muscle.

12. The method of claim 1, wherein completion of administering the effective amount of GABA results in an increase an amount of expression of myosin heavy chain (MHC) 2a.

13. The method of claim 1, wherein completion of administering the effective amount of GABA results in an increase a type I muscle fiber and/or a type IIa muscle fiber in a skeletal muscle of the subject in the physically active state when measured relative to the subject in the physically inactive state.

\* \* \* \* \*